United States Patent [19]

Hanze et al.

[11] 4,017,606

[45] Apr. 12, 1977

[54] ORGANIC COMPOUNDS AND PROCESS

[75] Inventors: Arthur R. Hanze, Kalamazoo; Gerald W. Camiener, Portage, both of Mich.

[73] Assignee: The Upjohn Company, Kalamazoo, Mich.

[22] Filed: Mar. 28, 1975

[21] Appl. No.: 563,043

Related U.S. Application Data

[60] Continuation of Ser. No. 403,676, Oct. 4, 1973, abandoned, which is a continuation of Ser. No. 169,535, Aug. 5, 1971, abandoned, which is a continuation of Ser. No. 870,155, June 27, 1969, abandoned, which is a division of Ser. No. 665,244, Sept. 5, 1967, Pat. No. 3,462,416, which is a continuation-in-part of Ser. No. 636,608, May 18, 1967, abandoned, which is a continuation-in-part of Ser. No. 612,331, Jan. 30, 1967, abandoned.

[52] U.S. Cl. .............................................. 424/180
[51] Int. Cl.$^2$ ...................................... A61K 31/70
[58] Field of Search ................. 424/180; 260/211.5

[56] References Cited

UNITED STATES PATENTS

| | | | |
|---|---|---|---|
| 3,328,388 | 6/1967 | Shen et al. ...................... | 260/211.5 |
| 3,444,294 | 5/1969 | Hunter .............................. | 424/180 |
| 3,462,416 | 8/1969 | Hanze et al. ................... | 260/211.5 |

OTHER PUBLICATIONS

Michelson, The Chemistry of Nucleosides and Nucleotides, (1963) Academic Press, N.Y., N.Y., pp. 27–29.

*Primary Examiner*—Norman A. Drezin
*Attorney, Agent, or Firm*—Martin B. Barancik; Roman Saliwanchik

[57] ABSTRACT

Novel hydrogenated pyrimidine nucleosides and nucleotides are produced by catalytic hydrogenation, particularly in the presence of a rhodium catalyst. The novel compounds are specifically used to inhibit deaminating enzymes, which would inactivate cytosine arabinoside by conversion to uridine arabinoside. Cytosine arabinoside is used for its anti-viral, particularly anti-herpes and anticytotoxic activity in mammals and birds, as well as to destroy phages which interfere with the production of antibiotics. Novel formulations containing cytosine arabinoside and the hydrogenated pyrimidine nucleosides are advantageous to provide prolonged cytosine arabinoside effects.

5 Claims, No Drawings

ORGANIC COMPOUNDS AND PROCESS

CROSS REFERENCE TO RELATED APPLICATIONS

This is a continuation of application, Ser. No. 403,676, filed Oct. 4, 1973, now abandoned which is a continuation of application Ser. No. 169,535, filed Aug. 5, 1971 and now abandoned, which is a continuation of Ser. No. 870,155, filed June 27, 1969, now abandoned, which is a divisional of Ser. No. 665,244, filed Sept. 5, 1967 and issued as U.S. 3,462,416, which is a continuation-in-part of Ser. No. 636,608, filed May 18, 1967, now abandoned, which is a continuation-in-part of Ser. No. 612,331, filed Jan. 30, 1967 and now abandoned.

BACKGROUND OF THE INVENTION

Field of the Invention

The present invention is concerned with new organic compounds and more particularly with novel reduced pyrimidine nucleosides and nucleotides, a process for the production thereof, and novel pharmaceutical and veterinary formulations.

SUMMARY OF THE INVENTION

The novel compounds and the process of production thereof can be illustratively represented by the following formulae:

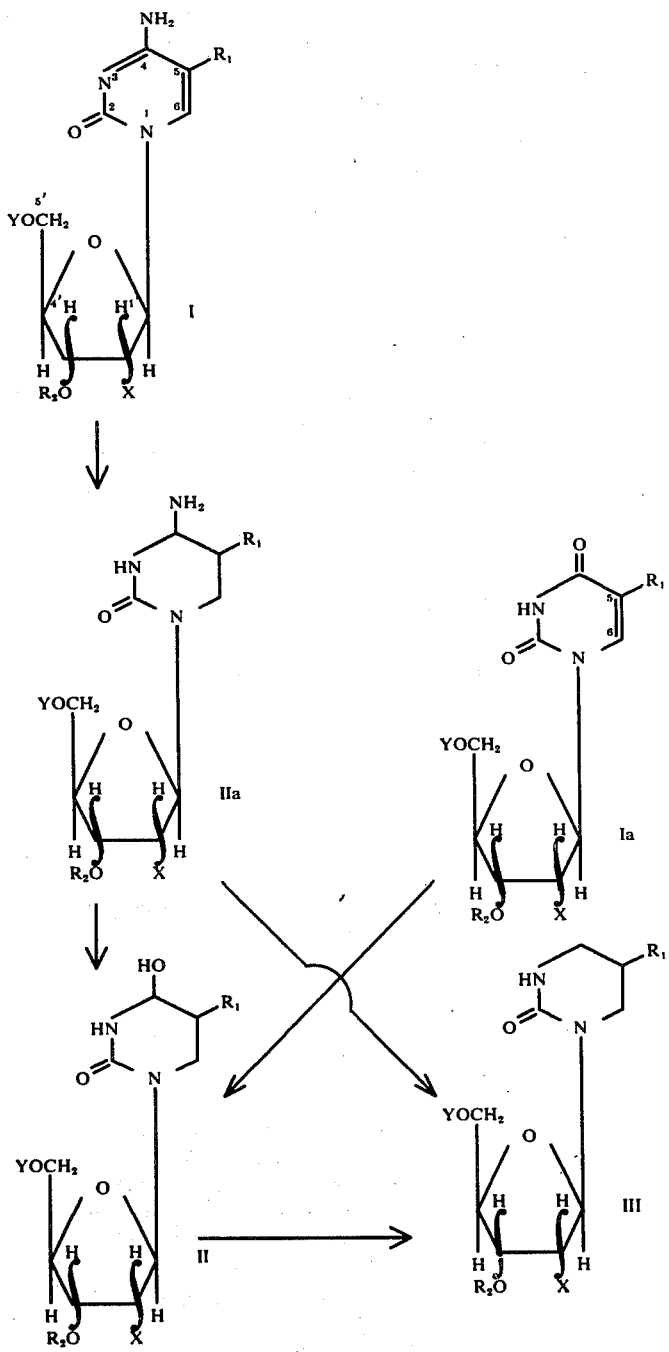

wherein $R_1$ is selected from the group consisting of hydrogen, methyl, hydroxymethyl, chlorine, fluorine and —$CF_3$; wherein $R_2$ is selected from the group consisting of hydrogen, Ac in which Ac is the acyl group of a hydrocarbon carboxylic acid containing from 2 to 12 carbon atoms, inclusive, and

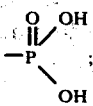

wherein X is selected from the group consisting of hydrogen, hydroxy, OAc in which Ac is defined as above, and

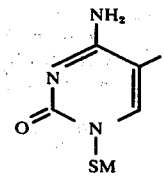

and wherein X and $OR_2$ together can be

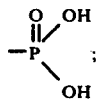

wherein Y is selected from the group consisting of hydrogen, Ac defined as above,

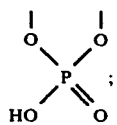

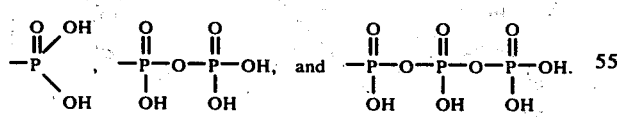

The process of the present invention comprises consecutively hydrogenating a pyrimidine nucleoside or acidification, of formula (1) or (1a) in the presence of a noble metal catalyst, e.g. a rhodium, palladium, or platinum catalyst, with from 2 to 3 molar equivalents of hydrogen per mole of starting compound. In the case of hydrogenation of cytosine compounds of formula (1), the uptake of 2 molar equivalents of hydrogen results in hydrogenation of the double bonds at 3,4, and 5,6 to yield compounds of formula (11a), which by mild acidificaion, for example to about pH 3 to 7, preferably to about pH 5 to 6, are hydrolyzed to compounds of formula (II) with liberation of ammonia. At this stage in the hydrogenation, small amounts of compounds of formula III are also present, which can be removed by partition chromatography or Craig distribution, if desired. Further hydrogenation gives increased yields of compounds of formula III.

Under the above-described hydrogenation conditions, only the pyrimidine moiety is hydrogenated remains stable] in a manner as follows:

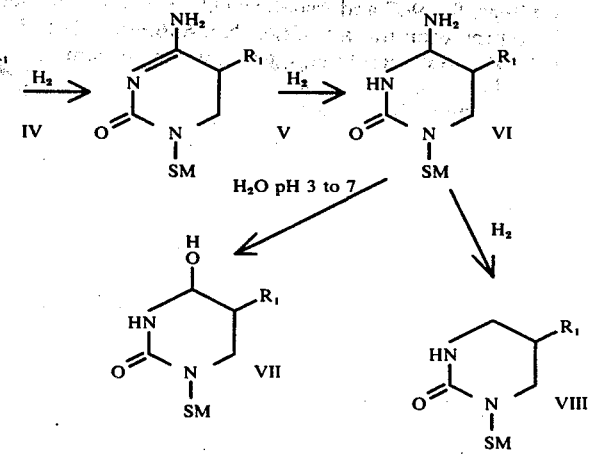

In the hydrogenation of uracil compounds (Ia), the hydrogenation reaction mixture is made basic by addition of ammonia or metal hydroxide and hydrogenation proceeds in a manner as follows:

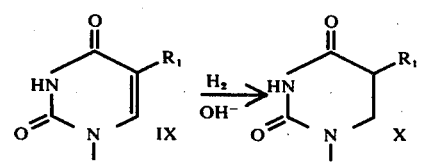

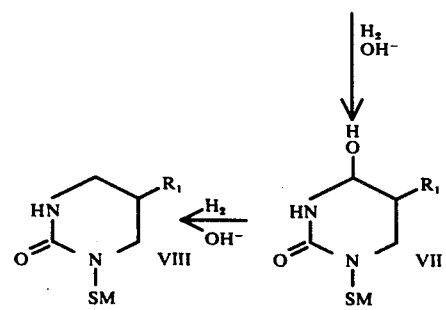

The sugar moiety (SM) as intended in the above formulae IV through X, includes the substituents $R_2$, Y and X of SM as defined earlier in formulae 1 to 111.

DESCRIPTION OF THE PREFERRED EMBODIMENTS

In the foregoing formulae, Ac signifies acyl groups of hydrocarbon carboxylic acids, e.g., of alkanoic acids such as acetic, propionic, butyric, isobutyric, valeric, isovaleric, hexanoic, heptanoic, octanoic, nonanoic, decanoic, undecanoic, dodecanoic acid and the like;

phenylalkanoic acids, e.g. benzoic, phenylacetic, 2- and 3-phenylpropionic acid and the like; unsaturated acids such as acrylic, crotonic, 1-hexenoic, 1-butynoic, 2-butynoic, undecylic, cinnamic acid, maleic acid and the like, cycloalkanoic acids e.g. cyclopentanecarboxylic acid cyclohexanecarboxylic acid, β-cyclopentylpropionic acid and the like.

The sugar moieties, in the unesterified form, herein used and configurationally represented in the prior formulae I to III are selected from the group consisting of:

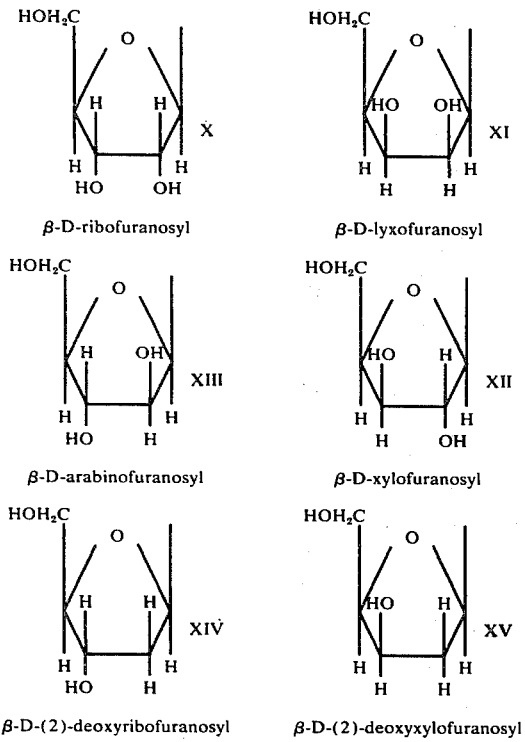

β-D-ribofuranosyl    β-D-lyxofuranosyl

β-D-arabinofuranosyl    β-D-xylofuranosyl

β-D-(2)-deoxyribofuranosyl    β-D-(2)-deoxyxylofuranosyl

The novel hydrogenated pyrimidine nucleosides and nucleotides of formulae II and IIa and the known compounds III are useful because of their ability to inhibit strongly the deamination of cytosine arabinoside (1-β-D-arabinofuranosylcytosine) and pharmaceutically acceptable derivatives thereof, by deaminase enzymes present in birds or mammals. Cytosine arabinoside is selectively active as a cytotoxic agent and has shown a wide spectrum of antitumor activity in mouse leukemias and ascites tumors. It has been become a preferred antileukemic agent in man, and is also useful in man in lymphosarcomas, with additional marginal activity shown in a limited number of solid tumors. It is also strongly antiviral, particularly against DNA viruses such as herpes, vaccinia, pseudorabies, swine pox, fowl pox, β-virus and adenoviruses, and can thus be used for preventing or controlling viral infection in mammals and birds. Cytosine arabinoside is also active against *Escherichia coli* and can be used to inhibit growth of this organism.

In the treatment of leukemia, cytosine arabinoside, usually as the hydrochloride salt, is administered by constant intravenous infusion at a rate of about 1 to 5 mg./kg. of body weight/day. Alternatively it is given by a single intravenous injection of about 10 to 50 mg./kg. of body weight every 7 to 14 days. Remission of myelogenous leukemia in adults as indicated by bone marrow response has been maintainined for more than 203 days by administering 1 to 5 mg./kg. weekly either intravenously or subcutaneously, whereas remission lasted for only 37 days without maintenance therapy. In the treatment of mammals for leukemia cytosine arabinoside may be given orally at dosages of about 10 to about 50 mg./kg.

In the past, therapeutic treatments with cytosine arabinoside, especially those in which the drug acts systemically, have been hampered by the deamination of cytosine arabinoside to the much less active uracil arabinoside in the animal. This is especially reflected in a drop in the blood level of cytosine arabinoside, usually concomitant with an increase in uracil arabinoside. This destruction of cytosine arabinoside is brought about by a deaminase enzyme present in the blood and tissues of the animal. It has unexpectedly been found that the novel compounds II and IIa of this invention, and the known compounds III, strongly inhibit such destruction. For example, deamination of cytosine arabinoside in rhesus monkey blood by liver deaminase was inhibited about 90% by the addition of one part of 4-hydroxyl-1-β-D-ribofuranosyl-tetrahydro-2(1H)-pyrimidinone (tetrahydrouridine) to 820 parts of cytosine arabinoside. In investigation in beagle dogs, treatment of the dogs with tetrahydrouridine at 100 mg./kg. by Intraveous injection, followed by similar administration of 50 mg./kg. of cytosine arabinoside, doubled the half life of cytosine arabinoside in the serum from 66–80 minutes in control dogs without tetrahydrouridine to 136–180 minutes in treated dogs, with no significant levels of uridine arabinoside in the serum or urine of treated dogs. Similar results have been achieved in monkey studies.

The novel compounds II and IIa and the known compound III, by impeding rapid degradation of cytosine arabinoside, permit treatment with cytosine arabinoside at either a lower dosage rate — thereby reducing any side effects of cytosine arabinoside—or, when at the same dosage rate, producing greater efficacy. The new compounds are therefore useful in combination with cytosine arabinoside in treatment of animals, e.g. pet monkeys or dogs affected with leukemia and possessing enzymes which deaminate the cytotoxic drug, cytosine arabinoside.

The novel compounds of formula IIa provide an especially desirable prolonged deamination-inhibition action, since in the animal body they are gradually converted to compounds of formula II by hydrolytic cleavage.

The inhibition of cytosine arabinoside deamination by a compound is conveniently expressed in terms of its competitive efficacy (C.E.). The competitive efficacy of a compound is determined as follows:

a. Standard curve.

Enzyme reaction mixture are prepared in 12-ml. centrifuge tubes in an ice bath. The tubes contain 1.0 micromole of tritiated Ca (specific activity, 5-microcuries per micromole), 250 micromoles of glycylglycin buffer at pH 8.0, 0.2 ml. of a centrifuged 25 percent homogenate of normal human liver prepared in Krebs-Ringer buffer modified by Camiener et. al. [Biochemical Pharmacology 14, 1405 (1965)] and distilled water to a final volume of 0.5 ml. This is the standard reaction mixture. In a series of comparable tubes, known amounts of untritiated Ca are added to the above standard reaction mixture. All tubes are incubated at 37° C. for 45 minutes. The tubes are then assayed for radioactive uracil arabinoside as described below, and the percent conversion of tritiated Ca to tritiated uracil arabinosie is calculated. A standard curve of the percent conversion vs. log$_{10}$ of the initial ratio of untritiated Ca to tritiated Ca is plotted. This is the standard curve for the C.E. test.

b. Reaction mixture for C.E. test.

To determine the C.E. of a compound, known amounts of the compound are added to the above standard reaction mixture and the percent conversion of tritiated Ca to tritiated uracil arabinoside is measured. This percent coversion is referred to the above standard curve to determine an euqivalent initial ratio of untritiated Ca to tritiated Ca under standard curve conditions. From this ratio and the amount of test compound in the assay reaction mixture, the C.E. is calculated.

For example, an assay reaction mixture containing 0.1 micromole of test compound gave 40 percent conversion of tritiated Ca to tritiated uracil arabinoside. From the assay standard curve, a 40 percent conversion was obtained in a standard curve reaction mixture at an initial ratio of untritiated Ca to tritiated Ca of 2:1. The C.E. of the compound thus is 2/0.1 or 20.

c. Assay for tritiated uracil arabinoside

After 45 minute incubation of the enzyme reaction mixtures, further reaction is stopped by the addition of one-half volume of iced, 15 percent trichloroacetic acid. The resulting precipitate is removed centrifugation. Suitable quantities (4 microliters) of clear supernatant solution are co-chromatographed with a mixture of 40 millimicromoles each of non-tritiated carrier Ca and uracil arabinoside on Whatman No. 40 paper. The papers are irrigated by the descending technic for 16 hours at room temperature with a developing solvent containing, by volumes, isopropanol 170, concentrated HCl 41, and water to 250. The Ca and uracil arabinosie zones are located by UV light, cut out and counted in a scintillation counter. Rf values are approximately as follows: Ca, 0.57; uracil arabinoside, 0.74. Percent conversion of tritiated Ca to tritiated uracil arabinoside is calculated from the counts.

The compounds of the invention are also useful in sustaining the effectiveness of cytosine arabinosides when the latter are used in fermentations to combat phage infections. For example, the highly useful antibiotic lincomycin is prepared commercially by fermentation of *Streptomyces lincolnensis* var. *lincolnensis* as described in U.S. Pat. No. 3,086,912. Such fermentations occasionally become infected by actinophages, which substantially and often completely prevents the production of lincomycin. Growth of the actinophages can be inhibited by adding cytosine arabinosie to the fermentation. However, the fermenting organism *S. lincolnensis* elaborates a deaminase which deaminates cytosine arabinoside to less effective uracil arabinosie. This deaminase can be inhibited by the addition of the compounds of this invention, advantageously by the addition of 4-hydroxy-1-β-D-ribofuranosyl-tetrahydro-2(1H)-pyrimidinone, to the fermentation along with cytosine arabinoside, and the production of lincomycin is sustained.

Some of the starting materials of this invention of formula I and Ia are found in nature such as thymidine, cytidine and uridine. Acyl derivatives, phosphates including di- and tri-phosphates of these compounds are easily prepared by the method shown in the book by A. M. Michaelson, The Chemistry of Nucleosides and Nucleotides, Academic Press, London and New York (1963); a generic way of making pyrimidine nucleosides is given by Jack J. Fox et al., J. Am. Chem. Soc. 78, 2117 (1956); Howard et al., J. Am. Chem. Soc. (1947) 1052–1054; Fox. J. Am. Chem. Soc. 73,3256 (1951); U.S. Pat. No.3,116,282 and the like.

In carrying out the process of the present invention, a compound of the formula I is hydrogenated in aqueous solution at room temperature in the presence of a rhodium catalyst for a prolonged period. The catalyst usually is on a carrier such as alumina, carbon, barium carbonate or calcium carbonate. Customarily, a Parr hydrogenator is used with an initial hydrogen pressure of from 25 to 60 pounds of hydrogen, but lower or higher pressures can be used and are operative. The catalysts from 2.5 to 10% rhodium-on-alumina are commercially available. Preferably, about a 5% rhodium or alumina catalyst is used. The ratio of this catalyst to the cytidine compound to be hydrogenated is about 1:5, but ratios between 1:2 up to 1:20 can be used. The time of hydrogenation under these conditions is about 5–48 hours, but from 16–24 hours are preferred. When approximately 1.7 to 2 molar equivalents of hydrogen have been taken up, the reaction mixture upon nuclear magnetic resonance examination shows evidence of hydrogenation of the 3,4 and 5,6 double bond with retention of the amino group at position 4. The thus-produced compounds of formula IIa may be isolated as dry solids by filtration and lyophilization of the reaction mixture. Since the thus-obtained products contain small amounts of compounds of formula III, they can be purified by such methods as Craig counter-current distribution, in the manner illustrated in Example 1, partition chromatography, or other methods common to the art. Compounds of formula II, having a hydroxyl group at position 4, may be obtained by acidifying the hydrogenation reaction mixture, or alternatively, by acidifying solutions containing compounds of formula IIa, to a pH range of about 3 to 7, preferably a pH range of 5 to 6, and holding this pH range for several hours, conveniently overnight. In this manner the compounds of formula IIa completely hydrolyze to compounds of formula II. Compounds of formula II can then be isolated from the reaction mixture by Craig distribution as exemplified in Example 1, column chromatography, or other methods of the art. To obtain compounds of formula III, the above-described reaction mixture containing essentially compound IIa can be filtered and, if desired, concentrated, and the solution hydrogenated further with the same amount of new catalyst, at the same temperature and hydrogenation pressure as before. When the total hydrogen uptake has reached about 2.5 to 3 molar equivalents, harvestable amounts of compounds of formula III are present. The compounds of formula III are isolated from the reaction mixture, wherein they are usually admixed with small amounts of compounds of formula II and other impurities, with the aid of Craig countercurrent distribution as illustrated in Example 1, column chromatography, or other suitable methods known in the art, and obtained as dry solids. For assurance of optimal yields of the desired compounds, the course of hydrogenation may be followed by analysis of periodic samples by nuclear magnetic resonance and detection and quantitation of the peaks characteristic of the compound desired, as given in standard references to nuclear magnetic resonance spectroscopy, such as Varian Associates, "NMR and EPR Spectroscopy", Pergamon Press, 1960. For example, production of 4-hydroxy-1-β-D-ribofuranosyl-tetrahydro-2(1H) pyrimidinone from uridine results in appearance of a multiplet peak at 5.12 ppm (referred to the peaks from sodium-2,2-dimethyl-2-silapentane-5-sulfonate (SDSS) as internal standard); this peak disappears on further hydrogenation to 1-β-D-ribofuranosyl-tetrahydro-2(1H)pyrimidinone.

If the starting material was a uridine of formula Ia, the same procedure is followed but, instead of water, dilute ammonium hydroxide or a dilute aqueous solution of a metal hydroxide is used, the concentration being about 0.1 to 0.01 N.

After the hydrogenation is completed, products are isolated and purfied by conventional methods such as by electrophoresis, chromatography or solvent extraction particularly with a Craig extraction apparatus.

The following examples are illustrative of the process and products of the present invention, but are not to be construed as limiting:

EXAMPLE 1

4-hydroxy-1-β-D-ribofuranosyl-tetrahydro-2-(1H)-pyrimidinone and
1-β-D-ribofuranosyl-tetrahydro-2(1H)-pyrimidinone from cytidine A solution of 7.85 g. (32.3 mmoles) of cytidine in 240 ml. of water was shaken in a Parr hydrogenator at 40 pounds of hydrogen pressure in the presence of 1.6 g. of 5% rhodium on alumina catalyst for a period of 20 hours. Approximately 2 molar equivalents of hydrogen were taken up. The solution was then filtered through a filter aid e.g. Celite, and the filtrate was concentrated at 35° under reduced pressure to yield 7.8 g. of a glassy semi-solid material. This solid was redissolved and hydrogenated again under the same conditions as above. After 20 hours of hydrogenation the pH of the solution was adjusted to approximately 5.5 and the solution kept at room temperature overnight. During this time IIa is converted to II. The solution was then concentrated to yield a syrup. The thus-obtained material (5 gm.) was placed in a Craig counter-current extraction apparatus having 500 tubes. The 5 g. were placed into 70 ml. of lower phase, the lower phase being water saturated with 2-butanol. The upper phase was 2-butanol saturated with water. After 2500 transfers, the weight of material in every tenth tube was determined and a curve plotted. On the basis of this curve the fractions which contained the desired materials were combined.

TABLE 1

| Fraction | Tube Nos. | Weight (mg.) | Competitive Efficacy |
|---|---|---|---|
| A | 120–170 | 340 | 250 |
| B | 190–230 | 210 | 560 |
| C | 310–320 | 110 | 7400 |
| D | 380–400 | 460 | 7400 |
| E | 460–500 | 490 | 200 |

According to nuclear magnetic resonance data, fractions C and D were 4-hydroxy-1-β-D-ribofuranosyl-tetrahydro-2(1H)-pyrimidinone, while fraction E was 1-β-D-ribofuranosyl-tetrahydro-2(1H)-pyrimidinone. Fractions C and D were lyophilized together to give 4-hydroxy-1-β-D-ribofuranosyl-tetrahydro-2(1H)-pyrimidinone as a white amorphous solid. In the same manner fraction E was lyophilized to give 1-β-D-ribofuranosyl-tetrahydro-2(1H)-pyrimidinone as a white solid. A sample of 4-hydroxy-1-β-D-ribofuranosyl-tetrahydro-2(1H)-pyrimidinone (II) was further purified by preparative paper chromatography. The material was streaked on 8 sheets of Whatman 3MM filter paper and developed in a solution of isopropyl alcohol: ammonium hydroxide: water (7:1:2). The material corresponding to II was cut out, eluted with water and the solution lyophilized. The resulting II was pure by nuclear magnetic resonance (NMR), papergram and analysis.

Analysis: Calcd. for $C_9H_{16}N_2O_6$ (248.24); C, 43.54; H, 6.49; N, 11.29. Found: C, 43.70; H, 6.38; N, 11.24.

The 1-β-D-ribofuranosyl-tetrahydro-2(1H)-one (III) obtained in fraction E was identical by NMR and IR spectroscopy and by thin layer chromatography with a sample prepared by the reduction of cytidine in water with hydrogen over a platinum catalyst.

Analysis: Calcd. for $C_9H_{16}N_2O_5$ (232.24); C, 46.60; H, 6.94; N, 12.05. Found: C, 46.24; H, 7.11; N, 12.04

EXAMPLE 2

4-hydroxy-1-β-D-ribofuranosyl-tetrahydro-2(1H-pyrimidinone and
1-β-D-ribofuranosyl-tetrahydro-2-(1H)-pyrimidinone from uridine A. 5,6-dihydrouridine A solution of 2.44 g. of uridine [1-β-D-ribofuranosyluracil] in 75 ml. of water was reduced at 40 pounds of hydrogen in the presence of 0.5 g. of 5% rhodium on alumina catalyst. The theoretical amount of hydrogen was absorbed in 24 hours. The mixture was filtered through a bed of diatomaceous earth (Celite) and concentrated to dryness. The crude material was crystallized from 40 ml. of methanol to give 1.87 g. of 5,6-dihydrouridine melting at 106°–108° C.

Analysis: Calcd. for $C_9H_{14}N_2O_6$: C, 43.90; H, 5.73; N, 11.38. Found: C, 43.39; H, 6.15; N, 10.89.

Ultraviolet: $\lambda_{max.}^{H_2O}$ sh 208 mu ($\epsilon$ 6600).

The 5,6-dihydrouridine structure is further supported by NMR and mass spectrum.

B. 4-hydroxy-1-β-D-ribofuranosyl-tetrahydro-2(1H)-pyrimidinone and 1-β-D-ribofuranosyl-tetrahydro-2(1H)-pyrimidinone from 5,6-dihydrouridine One and six tenths grams of the dihydrouridine obtained above in 60 ml. of water containing 0.6 ml. of concentrated ammonia was reduced with 0.5 g. of 5% rhodium on alumina in the presence of 42 pounds of hydrogen for a period of 18 hours. The resulting material was filtered to remove the catalyst, evaporated in vacuo and then extracted in a 500 tube Craig apparatus in a system consisting of 2-butanol-water as in Example 1. In this manner, 4-hydroxy-1-β-D-ribofuranosyl-tetrahydro-2(1H)-pyrimidinone and 1-β-D-ribofuranosyl-tetrahydro-2(1H)-pyrimidinone were obtained.

C. 4-hydroxy-1-β-D-ribofuranosyl-tetrahydro-2(1H)-pyrimidinone by sodium borohydride reduction of dihydrouridine To an ice cold solution of 246.2 mg. (1.0 mmole) of 5,6-dihydrouridine in 10 ml. of water at pH 7.5–8 was added 37.8 mg. (1.0 mmole-4.0 equivalents) of sodium borohydride. After 35 minutes the reaction mixture was set in a freezer overnight and put into an ice bath the next morning. The excess sodium borohydride was destroyed by addition of dilute acetic acid, the mixture was filtered and the filtrate lyophilized to give 4-hydroxy-1-β-D-ribofuranosyl-tetrahydro-2(1H)- pyrimidinone and a small amount of 1-β-D-ribofuranosyl-tetrahydro-2(1H)-pyrimidinone.

D. 4-hydroxy-1-β-D-ribofuranosyl-tetrahydro-2(1H)-pyrimidinone and 1-β-D-ribofuranosyl-tetrahydro-2(1H)-pyrimidinone from uridine.

In the manner given in Example 2B, uridine was directly reduced with a rhodium on alumina catalyst in a solvent medium consisting of 1 part concentrated ammonium hydroxide and 99 parts water to give 4-hydroxy-1-β-D-ribofuranosyl-tetrahydro-2(1H)-pyrimidinone and 1-β-D-ribofuranosyl-tetrahydro-2(1H)-pyrimidinone.

EXAMPLE 3

5-methyl-4-hydroxy-1-β-D-(2'-deoxy)ribofuranosyl-tetrahydro-2(1H)-pyrimidinone and
5-methyl-1-β-D-(2'-deoxy)ribofuranosyl-tetrahydro-2(1H)-pyrimidinone

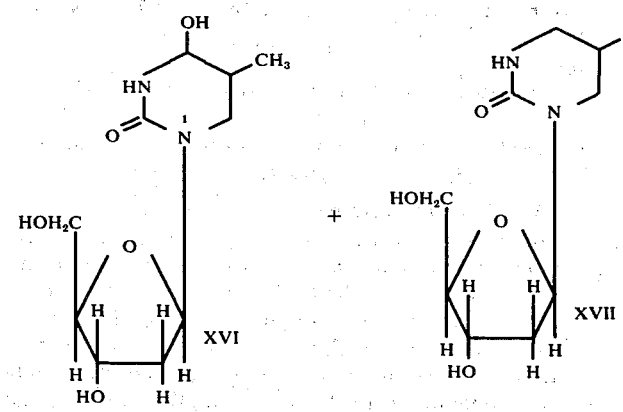

In the manner given in Example 2D, thymidine in ammoniacal water solution was hydrogenated twice consecutively in the presence of a rhodium on alumina catalyst and the product separated by a Craig extractor to give 5-methyl-4-hydroxy-1-β-D-(2'-deoxy)-ribofuranosyl-tetrahydro-2(1H)-pyrimidinone XVI and 5-methyl-1-β-D-(2'-deoxy)ribofuranosyl-tetrahydro-2(1H)-pyrimidinone XVII.

EXAMPLE 4

4-hydroxy-1-β-D-arabinofuranosyl-tetrahydro-2(1H)-pyrimidinone and
1-β-D-arabinofuranosyl-tetrahydro-2(1H)-pyrimidinone In the manner given in Example 1A 1-β-D-arabinofuranosyl-cytosine (U.S. Pat. No. 3,116,282) was hydrogenated in the presence of a rhodium on alumina catalyst to give 3,4,5,6-tetrahydro-cytosine arabinoside, hydrolyzed at pH 5–6 and separated with a Craig extractor to give 4-hydroxy-1-β-D-arabinofuranosyl-tetrahydro-2(1H)-pyrimidinone and 1-β-D-arabinofuranosyl-tetrahydro-2-(1H)-pyrimidinone.

EXAMPLE 5

5-fluoro-4-hydroxy-1-β-D-arabinofuranosyl-tetrahydro-2(1H)-pyrimidinone and
5-fluoro-1-β-D-arabinofuranosyl-tetrahydro-2(1H)-pyrimidinone In the manner given in Example 1, 1-β-D-arabinofuranosyl-5-fluorocytosine (U.S. Pat. No. 3,116,282) was hydrogenated in the presence of a rhodium on alumina catalyst, and the mixture hydrolyzed and separated with a Craig extractor to give 5-fluoro-4-hydroxy-1-β-D-arabinofuranosyl-tetrahydro-2(1H)-pyrimidinone and 5-fluoro-1-β-D-arabinofuranosyl-tetrahydro-2(1H)-pyrimidinone.

EXAMPLE 6

5-chloro-4-hydroxy-1-β-D-arabinofuranosyl-tetrahydro-2(1H)-pyrimidinone and
5-chloro-1-β-D-arabinofuranosyl-tetrahydro-2(1H)-pyrimidinone In the manner given in Example 1, 1-β-D-arabinofuranosyl-5-chlorocytosine (U.S. Pat. No. 3,116,282) was hydrogenated in the presence of a rhodium on alumina catalyst, and the mixture hydrolyzed and separated with a Craig extractor to give 5-chloro-1-β-D-arabinofuranosyl-tetrahydro-2(1H)-pyrimidinone

and 5-chloro-4-hydroxy-1-β-D-arabinofuranosyl-tetrahydro-2-(1H)-pyrimidinone.

EXAMPLE 7

5-ethoxy-4-hydroxy-1-β-D-arabinofuranosyl-tetrahydro-2(1H)-pyrimidinone and
5-ethoxy-1-β-D-arabinofuranosyl-tetrahydro-2(1H)-pyrimidinone In the manner given in Example 1D, 1-β-D-arabinofuranosyl-5-ethoxycytosine (U.S. Pat. No. 3,116,282) was hydrogenated in the presence of a rhodium on alumina catalyst, and the mixture hydrolyzed and separated with a Craig extractor to give 5-ethoxy-4-hydroxy-1-β-D-arabinofuranosyl-tetrahydro-2(1H)-pyrimidinone and 5-ethoxy-1-β-D-arabinofuranosyl-tetrahydro-2(1H)-pyrimidinone.

EXAMPLE 8

5-methoxy-4-hydroxy-1-β-D-arabinofuranosyl-tetrahydro-2(1H)-pyrimidinone and
5-methoxy-1-β-D-arabinofuranosyl-tetrahydro-2(1H)-pyrimidinone In the manner given in Example 1D, 1-β-D-arabinofuranosyl-5-methoxycytosine (U.S. Pat. No. 3,116,282) was hydrogenated in the presence of a rhodium on alumina catalyst, and the mixture hydrolyzed and separated with a Craig extractor to give 5-methoxy-4-hydroxy-1-β-D-arabinofuranosyl-tetrahydro-2(1H)-pyrimidinone and 5-methoxy-1-β-D-arabinofuranosyl-tetrahydro-2(1H)-pyrimidinone.

EXAMPLE 9

5-trifluoromethyl-4-hydroxy-1-β-D-arabinofuranosyl-tetrahydro-2(1H)-pyrimidinone and 5-trifluoromethyl-1-β-D-arabinofuranosyl-tetrahydro-2(1H)-pyrimidinone In the manner given in Example 1D, 1-β-D-arabinofuranosyl-5-trifluoromethylcytosine (U.S. Pat. No. 3,116,282) was hydrogenated in the presence of a rhodium on alumina catalyst, and the mixture separated with a Craig extractor to give 5-trifluoromethyl-4-hydroxy-1-β-D-arabinofuranosyl-tetrahydro-2(1H)-pyrimidinone and 5-trifluoromethyl-1-β-D-arabinofuranosyl-tetrahydro-2(1H)-pyrimidinone.

EXAMPLE 10

4-hydroxy-1-β-D-ribofuranosyl-tetrahydro-2(1H)-pyrimidinone and 1-β-D-ribofuranosyl-tetrahydro-2(1H)-pyrimidinone 2'-phosphates In the manner given in Example 2, uridine 2'-phosphate in ammoniacal water solution was hydrogenated twice consecutively in the presence of a rhodium on alumina catalyst and the product separated by a Craig extractor to give 4-hydroxy-1-β-D-ribofuranosyl-tetrahydro-2(1H)-pyrimidinone 2'-phosphate and 1-β-D-ribofuranosyl-tetrahydro-2(1H)-pyrimidinone 2'-phosphate.

EXAMPLE 11

4-hydroxy-1-β-D-ribofuranosyl-tetrahydro-2(1H)-pyrimidinone and 1-β-D-ribofuranosyl-tetrahydro-2(1H)-pyrimidinone 3'-phosphates In the manner given in Example 2D, uridine-3'-phosphate in ammoniacal water solution was hydrogenated in the presence of a rhodium on alumina catalyst and the product separated by a Craig extractor to give 4-hydroxy-1-β-D-ribofuranosyl-tetrahydro-2(1H)-pyrimidinone 3'-phosphate and 1-β-D-ribofuranosyl-tetrahydro-2(1H)-pyrimidinone 3'-phosphate.

EXAMPLE 12

5-hydroxymethyl-4-hydroxy-1-β-D-(2'-deoxy)-ribofuranosyl-tetrahydro-2(1H)-pyrimidinone 5'-phosphate and 5-hydroxymethyl-1-β-D-(2'-deoxy)ribofuranosyl-tetrahydro-2(1H)-pyrimidinone 5'-phosphate In the manner given in Example 2D 5-hydroxymethyl-(2'-deoxy)cytidine 5'-phosphate (The Chemistry of Nucleosides and Nucleotides, A. M. Michelson (1963, page 99) was hydrogenated in dilute ammonium hydroxide in the presence of a rhodium on alumina catalyst, and the mixture separated with a Craig extractor to give 5-hydroxymethyl-4-hydroxy-1-β-D-(2'-deoxy)-ribofuranosyl-tetrahydro-2(1H)-pyrimidinone 5'-phosphate and 5-hydroxymethyl-1-β-D-(2'-deoxy)-ribofuranosyl-tetrahydro-2(1H)-pyrimidinone 5'-phosphate.

EXAMPLE 13

4-hydroxy-1-β-D-arabinofuranosyl-tetrahydro-2(1H)-pyrimidinone 5'-phosphate and 1-β-D-arabinofuranosyl-tetrahydro-2(1H)-pyrimidinone 5'-phosphate In the manner given in Example 2D 1-β-D-arabinofuranosyl-cytosine 5'-phosphate [Cardeilhac et al., Cancer Research 24 1595 (1964)] was hydrogenated in dilute ammonium hydroxide in the presence of a rhodium on alumina catalyst, and the mixture separated with a Craig extractor to give 4-hydroxy-1-β-D-arabinofuranosyl-tetrahydro-2(1H)-pyrimidinone 5'-phosphate and 1-β-D-arabinofuranosyl-tetrahydro-2(1H)-pyrimidinone 5'-phosphate.

EXAMPLE 14

4-hydroxy-1-β-D-ribofuranosyl-tetrahydro-2(1H)-pyrimidinone 2'-phosphate and 1-β-D-ribofuranosyl-tetrahydro-2(1H)-pyrimidinone 2'-phosphate In the manner given in Example 2D 1-β-D-ribofuranosyl-uracil 2'-phosphate (The Chemistry of Nucleosides and Nucleotides, A. M. Michelson (1963) page 99) was hydrogenated in dilute ammonium hydroxide in the presence of a rhodium on alumina catalyst, and the mixture separated with a Craig extractor to give 4-hydroxy-1-β-D-ribofuranosyl-tetrahydro-2(1H)-pyrimidinone 2'-phosphate and 1-β-D-ribofuranosyl-tetrahydro-2(1H)-pyrimidinone 2'-phosphate.

EXAMPLE 15

3',5'-diphosphates of 5-methyl-4-hydroxy-1-β-D-(2'-deoxy)ribofuranosyl-tetrahydro-2(1H)-pyrimidinone and 5-methyl-1-β-D-(2'-deoxy)ribofuranosyl-tetrahydro-2(1H)-pyrimidinone

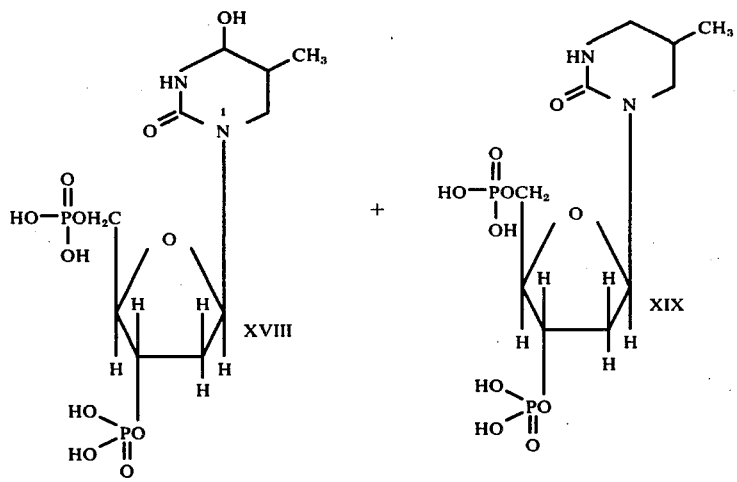

In the manner given in Example 2D, thymidine 3',5'-diphosphate (The Chemistry of Nucleosides and Nucleotides, A. M. Michelson (1963), page 110) in ammoniacal water solution was hydrogenated twice consecutively in the presence of a rhodium on alumina catalyst and the product separated by a Craig extractor to give the 3',5'-diphosphates of 5-methyl-4-hydroxy-1-β-D-(2'-deoxy)ribofuranosyl-tetrahydro-2(1H)-pyrimidinone (XVIII) and 5-methyl-1-β-D-(2'-deoxy)-ribofuranosyl-tetrahydro-2(1H)-pyrimidinone (XIX).

EXAMPLE 16

4-hydroxy-1-β-D-ribofuranosyl-tetrahydro-2(1H)-pyrimidinone 2',3'-cyclic phosphate and 1-β-D-ribofuranosyl-tetrahydro-2(1H)-pyrimidinone 2'-3'-cyclic phosphate In the manner given in Example 2D uridine 2',3'-cyclic phosphate [Michael Smith et al. J. Am. Chem. Soc. 80 6204 (1958)] in ammoniacal water solution was hydrogenated twice consecutively in the presence of a rhodium on alumina catalyst and the product separated by a Craig extractor to give 4-hydroxy-1-β-D-ribofuranosyl-tetrahydro-2(1H)-pyrimidinone 2',3'-cyclic phosphate and 1-β-D-ribofuranosyl-tetrahydro-2(1H)-pyrimidinone 2',3'-cyclic phosphate.

EXAMPLE 17

4-hydroxy-1-β-D-ribofuranosyl-tetrahydro-2(1H)-pyrimidinone 5'-pyrophosphate and 1-β-D-ribofuranosyl-tetrahydro-2(1H)-pyrimidinone 5'-pyrophosphate In the manner given in Example 2D, uridine 5'-pyrophosphate (Kenner et al., J. Chem. Soc., 3675, 1952) in ammoniacal water solution was hydrogenated twice consecutively in the presence of a rhodium on alumina catalyst and the product separated by a Craig extractor to give 4-hydroxy-1-β-D-ribofuranosyl-tetrahydro-2(1H)-pyrimidinone 5'-pyrophosphate and 1-β-D-ribofuranosyl-tetrahydro-2(1H)-pyrimidinone 5'-pyrophosphate.

EXAMPLE 18

4-hydroxy-1-β-D-ribofuranosyl-tetrahydro-2(1H)-pyrimidinone 5'-triphosphate and 1-β-D-ribofuranosyl-tetrahydro-2(1H)-pyrimidinone 5'-triphosphate In the manner given in Example 2D, uridine 5'-triphosphate (Kenner et al., J. Chem. Soc., 2288, 1954) in ammoniacal water solution was hydrogenated twice consecutively in the presence of a rhodium on alumina catalyst and the product separated by a Craig extractor to give 4-hydroxy-1-β-D-ribofuranosyl-tetrahydro-2(1H)-pyrimidinone 5'-triphosphate and 1-β-D-ribofuranosyl-tetrahydro-2(1H)-pyrimidinone 5'-triphosphate.

EXAMPLE 19

4-hydroxy-1-β-D-ribofuranosyl-tetrahydro-2(1H)-pyrimidinone 5'-phosphate and 1-β-D-ribofuranosyl-tetrahydro-2(1H)-pyrimidinone 5'-phosphate In the manner given in Example 2D, cytidine 5'-phosphate was hydrogenated in dilute ammonium hydroxide in the presence of a rhodium on alumina catalyst, and the mixture separated with a Craig extractor to give 4-hydroxy-1-β-D-ribofuranosyl-tetrahydro-2(1H)-pyrimidinone 5'-phosphate and 1-β-D-ribofuranosyl-tetrahydro-2(1H)-pyrimidinone 5'-phosphate.

EXAMPLE 20

4-hydroxy-1-β-D-ribofuranosyl-tetrahydro-2(1H)-pyrimidinone 5'-diphosphate and 1-β-D-ribofuranosyl-tetrahydro-2(1H)-pyrimidinone 5'-diphosphate In the manner given in Example 2D, cytidine 5'-diphosphate was hydrogenated in dilute ammonium hydroxide in the presence of a rhodium on alumina catalyst, and the mixture separated with a Craig extractor to give 4-hydroxy-1-β-D-ribofuranosyl-tetrahydro-2(1H)-pyrimidinone uridine 5'-diphosphate and 1-β-D-ribofuranosyl-tetrahydro-2(1H)-pyrimidinone 5'-diphosphate.

EXAMPLE 21

4-hydroxy-1-β-D-ribofuranosyl-tetrahydro-2(1H)-pyrimidinone 5'-triphosphate and
1-β-D-ribofuranosyl-tetrahydro-2(1H)-pyrimidinone 5'-triphosphate

EXAMPLE 24

5-methyl-4-hydroxy-1-β-D-(2'-deoxy)ribofuranosyl-tetrahydro-2(1H)-pyrimidinone 5'-triphosphate and
5-methyl-1-β-D-(2'-deoxy)ribofuranosyl-tetrahydro-2(1H)-pyrimidinone 5'-triphosphate

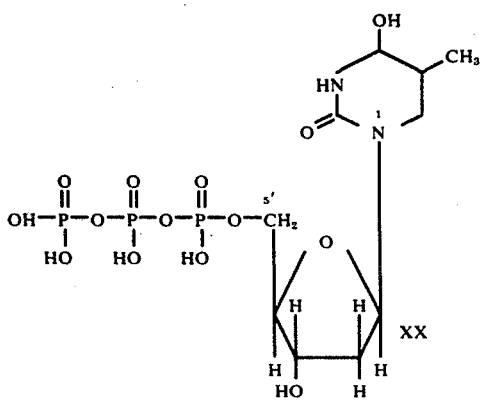

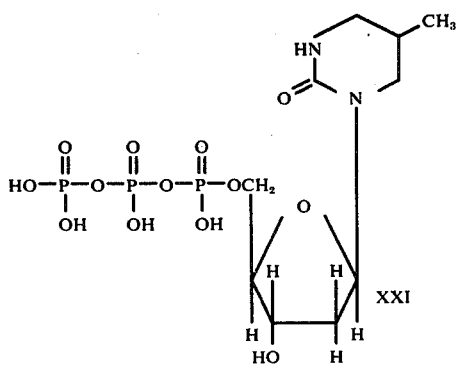

In the manner given in Example 2D cytidine 5'-triphosphate was hydrogenated in the presence of dilute ammonium hydroxide in the presence of a rhodium on alumina catalyst, and the mixture separated with a Craig extractor to give 4-hydroxy-1-β-D-ribofuranosyl-tetrahydro-2(1H)-pyrimidinone 5'-triphosphate and 1-β-D-ribofuranosyl-tetrahydro-2(1H)-pyrimidinone 5'-triphosphate.

EXAMPLE 22

4-hydroxy-1-β-D-ribofuranosyl-tetrahydro-2(1H)-pyrimidinone 5'-diphosphate 2',3'-di-O-acetate and
1-β-D-ribofuranosyl-tetrahydro-2(1H)-pyrimidinone 5'-diphosphate 2',3'-di-O-acetate In the manner given in Example 2 (a and c), uridine 5'-diphosphate 2',3'-di-O-acetate was hydrogenated in the presence of a rhodium on alumina catalyst, reduced with sodium borohydride, and the product separated by a Craig extractor to give 4-hydroxy-1-β-D-ribofuranosyl-tetrahydro-2(1H)-pyrimidinone 5'-diphosphate 2',-3'-di-O-acetate and 1-β-D-ribofuranosyl-tetrahydro-2(1H)-pyrimidinone 5'-diphosphate 2',3'-di-O-acetate.

EXAMPLE 23

4-hydroxy-1-β-D-ribofuranosyl-tetrahydro-2(1H)-pyrimidinone 5'-triphosphate 2',3'-di-O-phenylacetate and
1-β-D-ribofuranosyl-tetrahydro-2(1H)-pyrimidinone 5'-triphosphate 2',3'-di-O-phenylacetate In the manner given in Example 2 (a and c), uridine 5'-triphosphate, 2',3'-di-O-phenylacetate was hydrogenated in the presence of a rhodium on alumina catalyst, reduced with sodium borohydride and the product separated by a Craig extractor to give 4-hydroxy-1-β-D-ribofuranosyl-tetrahydro-2(1H)-pyrimidinone 5'-triphosphate 2',3'-di-O-phenylacetate and 1-β-D-ribofuranosyl-tetrahydro-2(1H)-pyrimidinone 5'-triphosphate 2',3'-di-O-phenylacetate.

In the manner given in Example 2D, thymidine 5'-triphosphate in ammoniacal water solution was hydrogenated twice consecutively in the presence of rhodium on alumina catalyst and the product separated by a Craig extractor to give 5-methyl-4-hydroxy-1-β-D-(2'-deoxy)ribofuranosyl-tetrahydro-2(1H)-pyrimidinone 5'-triphosphate (XX) and 5-methyl-1-β-D-(2'-deoxy)-ribofuranosyl-tetrahydro-2(1H)-pyrimidinone 5'-triphosphate (XXI).

EXAMPLE 25

5-chloro-4-hydroxy-1-β-D-ribofuranosyl-tetrahydro-2(1H)-pyrimidinone 5'-diphosphate and
5-chloro-1-β-D-ribofuranosyl-tetrahydro-2(1H)-pyrimidinone 5'-diphosphate In the manner given in Example 2D, 5-chlorouridine 5'-diphosphate [The Chemistry of Nucleosides and Nucleotides, A. M. Michelson, 1963, page 224; Michelson et al., Biochim. et Biophys. Acta 55, 529 (1962)] was catalytically hydrogenated in ammoniacal water, in the presence of rhodium on alumina to give 5-chloro-4-hydroxy-1-β-D-ribofuranosyl-tetrahydro-2(1H)-pyrimidinone 5'-diphosphate and 5-chloro-1-β-D-ribofuranosyl-tetrahydro-2(1H)-pyrimidinone 5'-diphosphate.

EXAMPLE 26

5-methyl-4-hydroxy-1-β-D-(2'-deoxy)ribofuranosyl-tetrahydro-2(1H)-pyrimidinone 3',5'-di-O-benzoate and
5-methyl-1-β-D(2'-deoxy)ribofuranosyl-tetrahydro-2(1H)-pyrimidinone 3',5'-di-O-benzoate In the manner given in Example 2 (A and C), thymidine 3',5'-di-O-benzoate [The Chemistry of Nucleosides and Nucleotides, A. M. Michelson 1963, page 84] was catalytically hydrogenated in the presence of rhodium on alumina and then reduced with sodium borohydride to give 5-methyl-4-hydroxy-1-β-D-(2'-deoxy)-ribofuranosyl-tetrahydro-2(1H)-pyrimidinone 3',5'-di-O-benzoate and 5-methyl-1-β-D-(2'-deoxy)ribofuranosyl-tetrahydro-2(1H)-pyrimidinone 3',5'-di-O-benzoate.

EXAMPLE 27

5-methyl-4-hydroxy-1-β-D-(2'-deoxy)xylofurano-tetrahydro-2(1H)-pyrimidinone

In the manner given in Example 2A, 1-β-D(2-deoxy)xylofuranosylthymine [The Chemistry of Nucleosides and Nucleotides, A. M. Michelson, 1963, page 69] was catalytically hydrogenated in water in the presence of a rhodium on alumina catalyst to give [1-β-D(2-deoxy)xylofuranosyl]dihydrothymine.

In the manner given in Example 2C [1-β-D(2-deoxy)xylofuranosyl] dihydrothymine was reduced with sodium borohydride to give 5-methyl-4-hydroxy-1-β-D(2'-deoxy)xylofurano-tetrahydro-2(1H)-pyrimidinone.

EXAMPLE 28

5-methyl-4-hydroxy-1-β-D-lyxofuranosyl-tetrahydro-2(1H)-pyrimidinone

In the manner given in Example 2A, 2-β-D-lyxofuranosyl-thymine [The Chemistry of Nucleosides and Nucleotides, A. M. Michelson, 1963, page 69] was catalytically hydrogenated in water in the presence of rhodium on alumina catalyst to give 1-β-D-lyxofurano-syl-dihydrothymine.

In the manner given in Example 2C 1-β-D-lyxofuranosyl-dihydrothymine was reduced with sodium borohydride to give 5-methyl-4-hydroxy-1-β-D-lyxofuranosyl-tetrahydro-2(1H)-pyrimidinone.

EXAMPLE 29

4-hydroxy-1-β-D-lyxofuranosyl-tetrahydro-2(1H)-pyrimidinone

In the manner given in Example 2A, 1-β-D-lyxofuranosyl-uracil [Fletcher et al., J. Am. Chem. Soc. 83, 1889 (1961)] was catalytically hydrogenated in water in the presence of rhodium on alumina catalyst to give 1-β-D-lyxofuranosyl-dihydrouracil.

In the manner given in Example 2C 1-β-D-lyxofuranosyl-dihydrouracil was reduced with sodium borohydride to give 4-hydroxy-1-β-D-lyxofuranosyl-tetrahydro-2(1H)-pyrimidinone.

EXAMPLE 30

5-fluoro-4-hydroxy-1-β-D-(2'-deoxy)ribofuranosyl-tetrahydro-2(1H)-pyrimidinone and
5-fluoro-1-β-D-(2'-deoxy)ribofuranosyl-tetrahydro-2(1H)-pyrimidinone In the manner given in Example 2D, 5-fluoro-2'-deoxyuridine [C. N. Yung et al., J. Am. Chem. Soc. 83,4060 (1961)] was catalytically hydrogenated in ammoniacal water in the presence of a rhodium on alumina catalyst to give 5-fluoro-4-hydroxy-1-β-D-(2'-deoxy)ribofuranosyl-tetrahydro-2(1H)-pyrimidinone and 5-fluoro-1-β-D-(2'-deoxy)ribofuranosyl-tetrahydro-2(1H)-pyrimidinone which were separated by extraction in a Craig apparatus.

EXAMPLE 31

5-fluoro-4-hydroxy-1-β-D-lyxofuranosyl-tetrahydro-2(1H)-pyrimidinone and
5-fluoro-β-D-lyxofuranosyltetrahydro-2(1H)-pyrimidinone In the manner given in Example 2D, 1-β-D-lyxofuranosyl-5-fluorouracil, [C. N. Yung et al., J. Am. Chem. Soc. 83, 4060 (1961)] was catalytically hydrogenated in ammoniacal water in the presence of a rhodium on alumina catalyst to give 5-fluoro-4-hydroxy-1-β-D-lyxofuranosyl-tetrahydro-2(1H)-pyrimidinone and 5-fluoro-1-β-D-lyxofuranosyl-tetrahydro-2(1H)-pyrimidinone which were separated by extraction in a Craig apparatus.

EXAMPLE 32

5-methyl-4-hydroxy-1-β-D-xylofuranosyl-tetrahydro-2(1H)-pyrimidinone and
5-methyl-1-β-D-xylofuranosyl-tetrahydro-2(1H)-pyrimidinone.

In the manner given in Example 2D, 1-β-D-xylofuranosylthymine [Fox et al., J. Am. Chem. Soc. 80, 5155 (1958)] was hydrogenated in ammoniacal water in the presence of a rhodium on alumina catalyst to give 5-methyl-4-hydroxy-1-β-D-xylofuranosyl-tetrahydro-2(1H)-pyrimidinone and 5-methyl-1-β-D-xylofuranosyl-tetrahydro-2(1H)-pyrimidinone.

EXAMPLE 33

5-methyl-4-hydroxy-1-β-D-xylofuranosyl-tetrahydro-2(1H)-pyrimidinone 2',3',5'-tribenzoate and
5-methyl-1-β-D-xylofuranosyl-tetrahydro-2(1H)-pyrimidinone 2',3',5'-tribenzoate In the manner given in Example 2 (A and C) but using as starting material 1-β-D-xylofuranosyl-thymine 2',3',5'-tribenzoate [Fox et al., Ibid.] yielded 5-methyl-4-hydroxy-1-β-D-xylofuranosyl-tetrahydro-2(1H)-pyrimidinone 2',3',5'-tribenzoate and 5-methyl-1-β-D-xylofuranosyl-tetrahydro-2(1H)-pyrimidinone 2',3',5'-tribenzoate.

In the same manner as shown in the before-mentioned Examples, esters of these nucleosides, and nucleotides such as acetates, propionates, butyrates, valerates, isovalerates, hexanoates, heptanoates, octanoates, nonanoates, decanoates, undecanoates, laurates, acrylates, crotonates, 1-hexenoates, undecylenoates, 1- and 2-butynoates, propynoates, 1- and 2-hexynoates, chrysanthemummonocarboxylates, β-cyclopentylpropionates, cyclohexanecarboxylates, benzoates, phenylacetates, α- and β-phenylpropionates, p-ethylbenzoates and the like, in positions 2',3' or 5' or combinations thereof, can be hydrogenated as in Example 2A, 2B or 2D to give the corresponding ester compounds of the before-mentioned hydrogenated nucleosides e.g. 5-hydroxymethyl-4-hydroxy-1-β-D-arabinofuranosyl-tetrahydro-2(1H)-pyrimidinone 2',3'-diacetate 5'-phosphate and 5-hydroxymethyl-1-β-D-arabinofuranosyl-tetrahydro-2(1H)-pyrimidinone 2',3',-diacetate 5'-phosphate; 4-hydroxy-1-β-D-ribofuranosyl-tetrahydro-2(1H)-pyrimidinone 5'-acetate 2',3'-cyclic phosphate and 1-β-D-ribofuranosyl-tetrahydro-2(1H)-pyrimidinone 5'-acetate 2',3'-cyclic phosphate; 4-hydroxy-1-β-D-(2'-deoxy)ribofuranosyl-tetrahydro-2(1H)-pyrimidinone 5'-benzoate 3'-phosphate and 1-β-D-(2'-deoxy)ribofuranosyl-tetrahydro-2(1H)-pyrimidinone 5'-benzoate 3'-phosphate; 5-methyl-4-hydroxy-1β-D-lyxofuranosyl-tetrahydro-2(1H)-pyrimidinone 2',3'-cyclic phosphate 5'-cyclohexanecarboxylate; 5-hydroxymethyl-4-hydroxy-1-β-D-ribofuranosyl-tetrahydro-2(1H)-pyrimidinone 5'-crotonate 2',3'-cyclic phosphate and 5-hydroxymethyl-1-β-D-ribofuranosyl-tetrahydro-2(1H)-pyrimidinone 5'-crotonate 2',3'-cyclic phosphate; 5-methyl-4-hydroxy-1-(2',3'-di-O-β-cyclopentylpropionyl)-β-D-xylofuranosyl-5'-triphosphate, 5-fluoro-4-hydroxy-1-[2',3'-di-O-

(1-butynoyl)-β-D-xylofuranosyl]-tetrahydro-2(1H)-pyrimidinone 5'-pyrophosphate and 5-fluoro-1-[2',3'-di-O-(1-butynoyl)-β-D-xylofuranosyl]-tetrahydro-2(1H)-pyrimidinone 5'-pyrophosphate; 5-chloro-4-hydroxy-1-β-D-arabinofuranosyl-tetrahydro-2(1H)-pyrimidinone 2',3',5'-tricrotonate and 5-chloro-1-β-D-arabinofuranosyl-tetrahydro-2(1H)-pyrimidinone 2',-3',5'-tricrotonate and the like.

Other tetrahydro- and hexahydropyrimidino nucleosides and nucleotides can be produced by reducing the nucleosides or nucleotide catalytically (Example 2a) to the dihydrouridine nuceloside or nucleotide followed by reduction with sodium borohydride (Example 2C). Representative compounds thus obtained include:

4-hydrox-1-β-D-arabinofuranosyl-tetrahydro-2(1H)-pyrimidinone 2',3'-diacetate and 1-β-D-arabinofuranosyl-tetrahydro-2(1H)-pyrimidinone 2',3'-diacetate;

5-trifluoromethyl-4-hydroxy-1-β-D-ribofuranosyl-tetrahydro-2(1H)-pyrimidinone 2',3',5'-tribenzoate and 5-trifluoromethyl-1-β-D-ribofuranosyl-tetrahydro-2(1H)-pyrimidinone 2',3',5'-tribenzoate;

5-chloro-4-hydroxy-1-β-D-(2'-deoxyl)ribofuranosyl-tetrahydro-2(1H)-pyrimidione 2',3',5'-tri-O-phenylacetate and 5-chloro-1-β-D-(2'-deoxy)ribofuranosyl-tetrahydro-2(1H)-pyrimidinone 2',3',5'-tri-O-phenylacetate;

5-methyl-4-hydroxy-1-β-ribofuranosyl-tetrahydro-2(1H)-pyrimidinone 2',3'-di-O-phenylpropionate and 5-methyl-1-β-D-ribofuranosyl-tetrahydro-2(1H)-pyrimidinone 2',3'-di-O-phenylpropionate;

5-ethyl-4-hydroxy-1-β-D-arabinofuranosyl-tetrahydro-2(1H)-pyrimidinone 2',3'-dilaurate 5'-phosphate and 5-ethyl-1-β-D-arabinoforanosyl-tetrahydro-2(1H)-pyrimidinone 2',3'-dilaurate 5'-phosphate;

4-hydroxy-1-β-D-xylofuranosyl-tetrahydro-2(1H)-pyrimidione 2',3'-diacrylate 5'-phosphate and 1-β-D-xylofuranosyl-tetrahydro-2(1H)-pyrimidinone 2',3'-diacrylate 5'-phosphate;

5-chloro-4-hydroxy-1-β-D-(2'-deoxy)xylylfuranosyl-tetrahydro-2(1H)-pyrimidinone 3',5'-diphosphate and 5chloro-1-β-D(2-deoxy)-xylylfuranosyl-tetrahydro-2(1H)-pyrimidinone 3',5'-diphosphate and the like.

EXAMPLE 34

4-amino-1-β-D-ribofuranosyl-tetrahydro-2(1H)-pyrimidinone

A solution of 17.5 g. (72 millimoles) of cytidine in 540 ml. of water was hydrogenated in a Parr hydrogenator at 30 psi pressure, in the presence of 3.6 g. of 5% rhodium on alumina catalyst. Hydrogen uptake overnight (18–19 hours) was approximately 2 molar equivalents. The solution (pH 10.5) was filtered through a bed of Celite (diatomaceous earth) filter and lyophilized to yield 4-amino-1-β-D-ribofuranosyl-tetrahydro-2(1H)-pyrimidinone as a white amorphous solid. When examined by nuclear magnetic resonance the solid showed a doublet at 5.95 ppm. (anomeric proton); multiplet at 4.50 ppm.

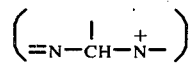;

multiplets at 3.45 ppm. (—CH₂N=) and 2.00 ppm. (C—CH₂—C) and a small amount of absorption at 2.75 ppm.

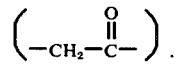.

Upon acidification, the 4.50 ppm. multiplet moved downfield to 5.08 ppm.

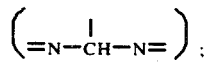

and part of the 2.00 ppm. multiplet moved slightly downfield to 2.2 ppm. Peak locations are referred to the peak for sodium-2,2-dimethyl-2-silapentane-5-sulfonate (SDSS) as internal standard. Held in aqueous solution at pH 5.5 to 6 overnight, the solid was converted to and gave the analytical characteristics of 4-hydroxy-1-β-D-ribofuranosyl-tetrahydro-2(1H)-pyrimidinone.

Formulation of cytosine arabinoside and compounds of formula II, IIa or III for oral, intravenous and intramuscular treatment can be prepared, the dosage being dependent on age, weight and condition of the subject being treated, the severity of the particular condition, the frequency of administration and the route of administration. Suitable pharmaceutically acceptable diluents are used for the preparation of such formulations.

Pharmaceutically acceptable diluent means a compatible, nontoxic material suited for compounding combinations of the principal active ingredients. In combinations of the principal active ingredients for parenteral use, such as intramuscularly, intravenously, and by regional perfusion, the diluent can be a sterile aqueous vehicle containing a preservative; for example, methylparaben, propylparaben, phenol, and chlorobutanol. The aqueous vehicle can also contain sodium chloride, preferably in an amount to be isotonic, as well as a suspending agent, for example, methylcellulose and polyvinylpyrrolidone; and a surfactant, for example, polysorbate 80. 100% and 50% aqueous dimethylacetamide are operable diluents in parenteral use combinations, which can be suitably further diluted extemporaneously with sterile aqueous vehicles. Similarly, aqueous solutions and suspensions can be compounded for oral use.

A finely divided powder, preferably micronized, comprising the principal active ingredients, suitably diluted with lactose, for example, is also prepared for local use. For oral administration, capsules, suitably containing appropriate diluents, for example, lactose, starch, magnesium stearate, and the like, can also be prepared. Likewise, there can be prepared a tablet suitably compounded as required with the above-mentioned appropriate pharmaceutical diluents.

The inventive pharmaceutical compositions are administered in varying dosages, depending upon the weight and condition of the mammals or birds to be treated; the route of administration, for example, oral, parenteral, or local and the nature of the desired result.

Dosage forms for either oral or parenteral use may contain cytosine arabinoside to give about 0.1 to about 50 mg. per kg. of body weight and compounds of formula II, IIa and III in a ratio of from about 1 part compound per 1000 parts of cytosine arabinoside to about 10 parts of compound per 1 part of cytosine arabinoside in a single dose.

In pharmaceutical preparations for local use in afflicted mammals following surgical removal of a tumor, concentrations of each of the principal ingredients may range from about 0.1 to about 10% by weight, the ratio of compound of formula II, IIa or III to cytosine arabinoside being from about 1:1000 to about 10:1.

The following examples set forth the manner and process of making and using the inventive compositions and include the best mode contemplated by the inventor(s).

EXAMPLE 35

Tablets 1000 tablets for oral use, each containing 300 mg. of cytosine arabinoside and 300 mg. of tetrahydrouridine are prepared from the following ingredients:

| | |
|---|---|
| Cytosine arabinoside | 300 Gm. |
| Tetrahydrouridine | 300 Gm. |
| Starch, U.S.P. | 35 Gm. |
| Talc, U.S.P. | 25 Gm. |
| Calcium stearate | 3.5 Gm. |

The powdered active ingredients are granulated with a 4% w/v aqueous solution of methylcellulose U.S.P. To the dried granules is added a mixture of the remainder of the ingredients and the final mixture is compressed into tablets of proper weight.

Similarly, tablets containing 500 mg. of cytosine arabinoside and 10 mg. of tetrahydrouridine are prepared by using 500 Gm. of cytosine arabinoside and 10 Gm. of tetrahydrouridine.

EXAMPLE 36

Hard capsules 1000 two-piece hard gelatin capsules for oral use each containing 100 mg. of 4-Amino-1-$\beta$-D-ribofuranosyl-tetrahydro-2(1H)-pyrimidinone and 100 mg. of cytosine arabinoside hydrochloride, are prepared from the following ingredients:

| | |
|---|---|
| 4-Amino-1-$\beta$-D-ribofuranosyl-tetrahydro-2(1H)-pyrimidinone | 100 Gm. |
| Cytosine arabinoside hydrochloride | 100 Gm. |
| Corn starch, U.S.P. | 150 Gm. |
| Light mineral oil, U.S.P. | 15 Gm. |
| Magnesium stearate powder | 15 Gm. |
| Talc, U.S.P. | 15 Gm. |

The materials are mixed throughly and encapsulated.

EXAMPLE 37

Syrup

A syrup for oral use, containing 125 mg. of cytosine arabinoside hydrochloride and 125 mg. of 1-$\beta$-D-ribofuranosyl-tetrahydro-2(1H)-pyrimidinone in each teaspoonful (5 ml.) is prepared from the following ingredients:

| | |
|---|---|
| Cytosine arabinoside hydrochloride | 25 Gm. |
| 1-$\beta$-D-ribofuranosyl-tetrahydro-2(1H)-pyrimidinone | 25 Gm. |
| Preservative | 2.5 Gm. |
| Glycerin, U.S.P. | 150 ml. |

-continued

| | |
|---|---|
| Tragacanth powder, U.S.P. | 7.5 Gm. |
| Flavor | 0.2 ml. |
| Sucrose, U.S.P. | 400 Gm. |
| Purified water q.s. | 1000 ml. |

EXAMPLE 38

Injectable solution

A sterile aqueous solution suitable for intramuscular or intravenous use, and containing 250 mg. of cytosine arabinoside hydrochloride and 0.5 mg. of tetrahydrouridine in each ml., is prepared from the following ingredients:

| | |
|---|---|
| Cytosine arabinoside hydrochloride | 250 Gm. |
| Tetrahydrouridine | 0.5 Gm. |
| Water for injection q.s. | 1000 ml. |

EXAMPLE 39

Injectable preparation

A sterile aqueous preparation suitable for intramuscular injection and containing 25 mg. of cytosine arabinoside hydrochloride and 1 mg. of tetrahydrouridine in each ml., is prepared from the following ingredients:

| | |
|---|---|
| Cytosine arabinoside hydrochloride | 25 Gm. |
| Tetrahydrouridine | 1 Gm. |
| Polyethylene glycol 4000, U.S.P. | 30 Gm. |
| Sodium Chloride, U.S.P. | 9 Gm. |
| Preservative q.s. | |
| Water for injection q.s. | 1000 ml. |

We claim:

1. A pharmaceutical preparation comprising:
   a. 1-$\beta$-D-arabinofuranosylcytosine or a pharmaceutically acceptable acid addition salt thereof, and
   b. A compound of the formula:

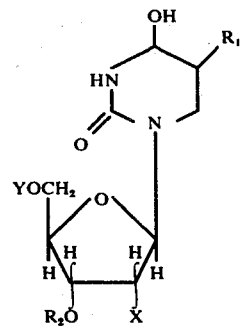

II wherein $R_1$ is selected from the group consisting of hydrogen, methyl, hydroxymethyl, chlorine, fluorine and —$CF_3$; wherein $R_2$ is selected from the group consisting of hydrogen, Ac in which Ac is the acyl group of a hydrocarbon carboxylic acid containing from 2 to 12 carbon atoms, inclusive, and

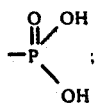

wherein X is selected from the group consisting of hydrogen, hydroxy, OAc in which Ac is defined as above, and

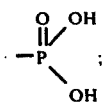

and wherein X and OR₂ together can be

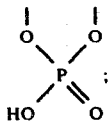

wherein Y is selected from the group consisting of hydrogen, Ac defined as above,

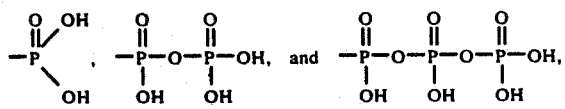

wherein the ratio of 1-β-D-arabinofuranosylcytosine to the compound selected from (b) above is between 1,000:1 and 1:10.

2. A pharmaceutical formulation according to claim 1, wherein the compound selected from (b) is tetrahydrouridine.

3. A pharmaceutical formulation according to claim 2 further containing a pharmaceutically acceptable carrier.

4. A pharmaceutical formulation as an oral unit dosage form containing from 1 to 500 mg. of 1-β-D-cytosine arabinoside and a compound of the formula:

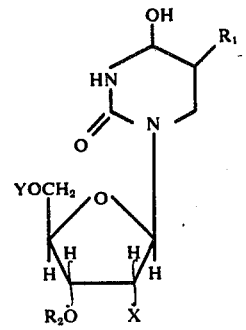

II wherein R₁ is selected from the group consisting of hydrogen, methyl, hydroxymethyl, chlorine, fluorine and —CF₃; wherein R₂ is selected from the group consisting of hydrogen, Ac in which Ac is the acyl group of a hydrocarbon carboxylic acid containing from 2 to 12 carbon atoms, inclusive, and

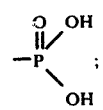

wherein X is selected from the group consisting of hydrogen, hydroxy, OAc in which Ac is defined as above, and

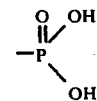

and wherein X and OR₂ together can be

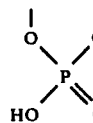

wherein Y is selected from the group consisting of hydrogen, Ac defined as above,

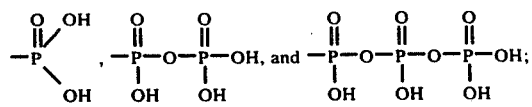

in a ratio between 1,000:1 and 1:10, and a pharmaceutically acceptable carrier.

5. A pharmaceutical formulation as an oral unit dosage form containing from 1 to 500 mg. of 1-β-D-cytosine arabinoside and tetrahydrouridine in a ratio between 1,000:1 to 1:10.

* * * * *